United States Patent
Huang et al.

(10) Patent No.: US 8,641,900 B2
(45) Date of Patent: Feb. 4, 2014

(54) METHOD AND DEVICE FOR CONTINUOUSLY PREPARING MICROSPHERES, AND COLLECTION UNIT THEREOF

(75) Inventors: Shou-Min Huang, Taoyuan (TW); Chun-Wei Liu, Taoyuan (TW); Kuo-Hua Yang, Taoyuan (TW)

(73) Assignee: Taiwan Biotech Co., Ltd, Taoyuan (TW)

( * ) Notice: Subject to any disclaimer, the term of this patent is extended or adjusted under 35 U.S.C. 154(b) by 483 days.

(21) Appl. No.: 12/939,460

(22) Filed: Nov. 4, 2010

(65) Prior Publication Data
US 2011/0101553 A1    May 5, 2011

Related U.S. Application Data

(60) Provisional application No. 61/258,230, filed on Nov. 5, 2009.

(30) Foreign Application Priority Data

Oct. 11, 2010    (TW) ............................... 99134644 A

(51) Int. Cl.
*A61K 9/50*    (2006.01)
(52) U.S. Cl.
USPC .............................................. 210/285; 264/4
(58) Field of Classification Search
USPC .......... 209/155, 156, 17; 264/4, 4.1; 210/285, 210/521
See application file for complete search history.

(56) References Cited

U.S. PATENT DOCUMENTS

| | | | |
|---|---|---|---|
| 2,236,895 A * | 4/1941 | Court | 210/773 |
| 3,502,211 A * | 3/1970 | Polnitz et al. | 210/791 |
| 4,994,281 A | 2/1991 | Muranishi et al. | |
| 5,656,299 A | 8/1997 | Kino et al. | |
| 5,770,231 A | 6/1998 | Mesens et al. | |
| 5,792,477 A | 8/1998 | Rickey et al. | |
| 5,871,778 A | 2/1999 | Kino et al. | |
| 5,945,126 A | 8/1999 | Thanoo et al. | |
| 6,194,006 B1 | 2/2001 | Lyons et al. | |
| 6,224,794 B1 | 5/2001 | Amsden et al. | |
| 6,296,842 B1 | 10/2001 | Jaworowicz et al. | |

(Continued)

FOREIGN PATENT DOCUMENTS

TW    I225416    12/2004

OTHER PUBLICATIONS

Lin et al, "Conduction Compressible Fluid", Publication Date. 2002, pp. 21-22.

*Primary Examiner* — Galen Hauth
(74) *Attorney, Agent, or Firm* — Rabin & Berdo, P.C.

(57) ABSTRACT

A method and a device for continuously preparing microspheres, and a collection unit thereof are provided. The collection unit for collecting microspheres in the solution comprises a tank and a first plate. The first plate is removably disposed in the tank. The first plate, when lay across the tank, has its two ends came in contact with the sidewall of the tank so as to divide the tank into a first chamber and a second chamber. The tank has an outlet located in the second chamber. After the solution with microspheres are input to the first chamber of the tank, the microspheres are deposited around the first plate, and the solution is caused to pass through or over the first plate to the second chamber and output from the outlet.

13 Claims, 9 Drawing Sheets

(56) References Cited

U.S. PATENT DOCUMENTS 6,361,798 B1  3/2002  Thanoo et al.
6,440,493 B1 * 8/2002 Gibson et al. .............. 427/213.3
2007/0182040 A1 * 8/2007 Suzuki et al. .................. 264/4.1

* cited by examiner

| Time | Drug release efficiency |
|---|---|
| 1 Hour | 1.09% |
| 2 Hour | 1.98% |
| 4 Hour | 2.72% |
| 1 day | 6.42% |
| 2 day | 8.56% |
| 3 day | 10.01% |
| 7 day | 16.94% |
| 14 day | 23.61% |
| 28 day | 35.92% |
| 56 day | 58.04% |

FIG. 10A

| Time | Drug release efficiency |
|---|---|
| 1 Hour | 4.26% |
| 2 Hour | 7.35% |
| 4 Hour | 10.58% |
| 8 Hour | 15.74% |
| 1 day | 36.23% |
| 2 day | 5642% |
| 3 day | 74.3% |
| 4 day | 85.62% |
| 5 day | 93.03% |

FIG. 11A

METHOD AND DEVICE FOR CONTINUOUSLY PREPARING MICROSPHERES, AND COLLECTION UNIT THEREOF

This application claims the benefit of U.S. provisional application Ser. No. 61/258,230, filed Nov. 5, 2009, and Taiwan application Serial No. 99134644, filed Oct. 11, 2010, the subject matter of which is incorporated herein by reference.

BACKGROUND OF THE INVENTION

1. Field of the Invention

The invention relates in general to a method and a device for preparing microspheres as well as a collection unit thereof, and more particularly to a method and a device for preparing microspheres in a continuous manner as well as a collection unit thereof.

2. Description of the Related Art

Microcapsules and Microspheres formed from various natural or synthetic polymers and resins have become popular delivery vehicles for various active materials such as drugs, diagnostic reagents, and the like. Biodegradable microcapsules and microspheres are for use in so called depot formulations, where delivery of the active material over an extended period of time is desired.

Processes for preparing microspheres usually involve the formation of at least one dispersed phase in a continuous phase. The dispersed phase usually includes the active material and polymer and, upon solidification in the continuous phase, becomes a microsphere. Microcapsules are similarly formed using multiple phases. In a conventional practice, a water-oil-water (w/o/w) emulsion is formed, and the polymer caused to precipitate out of one phase onto the surface of a dispersed phase to form a capsule wall thereon upon solidification of the polymer.

In 1980, a biodegradable polymer, poly(lactic/glycolic acid) (PLGA), was first developed and utilized to encapsulate leuprolide acetate, by Takeda pharmaceutical company, Japan. In the process of preparing product, sustained-release microcapsules, in which a water-oil-water (w/o/w) double emulsion is used to encapsulate drugs, are employed. In the process of solidifying microcapsules, the drugs and the first emulsion of PLGA are introduced into polyvinyl alcohol (PVA) where the PLGA is emulsified at the second time, and the capsules are solidified by drying in liquid process.

Because there will be drugs and PVA remained on the surface of the microcapsules, clean water is usually mixed in to clean the microcapsules, and the microcapsules are collected by centrifugalization. However, the capsules with PLGA polymer do not have enough hardness, which causes the problems of deformation and aggregation of capsules after centrifugalization.

Moreover, centrifugally collecting capsules is required to be operated by personnel. Operation process thereof includes: distributing the solidified microcapsules and solution into several centrifugal tubes; carefully removing the supernatant from each tube after centrifugalization; introducing a small amount of certain solution so as to suspend the microcapsules again; collecting the microcapsules; and making the microcapsules into powder by drying. The conventional process in fact belongs to a batch process, which requires an operator to manipulate the centrifugal machine to complete the steps of collecting microcapsules, thereby increasing manufacturing cost, failing to establish a continuous preparing process due to its collecting behavior, and causing a limit to production scale thereof. Furthermore, the produced microcapsules have the problem of deformation or aggregation, which also negatively affects the release model of drugs.

SUMMARY OF THE INVENTION

The invention is directed to a method and a device for continuously preparing microspheres as well as a collection unit thereof, wherein the microspheres are collected by a nature process of deposition, which prevents the problems of deformation and aggregation of the microspheres, makes it possible to continuously collect the microspheres, and establishes a process for continuously preparing the microspheres.

According to a first aspect of the present invention, a collection unit is provided for collecting a number of microspheres in a solution. The collection unit comprises a tank and a first plate. The tank has an outlet. The first plate is removably disposed in the tank. When being lay across the tank, the first plate has its two ends came in contact with the sidewall of the tank so as to divide the tank into a first chamber and a second chamber. The outlet is located in the second chamber. After the solution containing the microspheres is input to the tank through the first chamber, the microspheres are deposited around the first plate, and the solution is caused to pass through or over the first plate to the second chamber and output from the outlet.

According to a second aspect of the present invention, a device is provided for continuously preparing microspheres. The device comprises a material supply unit, an emulsification unit, a solidification unit, and an aforementioned collection unit. The material supply unit is for independently and continuously providing an aqueous solution and an organic solution. The aqueous solution contains a surfactant, and the organic solution contains an active material and a degradable polymeric material. The emulsification unit is for accepting the aqueous solution and the organic solution and mixing the aqueous solution with the organic solution to obtain an emulsification solution. The emulsification solution contains a number of microspheres formed by combining the degradable polymeric material with the active material. The solidification unit is for accepting the emulsification solution and mixing the emulsification solution with a solidification solution, so as to solidify the microspheres. The collection unit comprises a tank and a first plate. The tank has an outlet. The first plate is removably disposed in the tank. When being lay across the tank, the first plate has its two ends came in contact with the sidewall of the tank so as to divide the tank into a first chamber and a second chamber. The outlet is located in the second chamber. After the solution containing the microspheres is input to the tank through the first chamber, the microspheres are deposited around the first plate, and the solution is caused to pass through or over the first plate to the second chamber and output from the outlet.

According to a third aspect of the present invention, a method is provided for continuously preparing microspheres. The method comprising: (a) providing an aqueous solution containing an surfactant; (b) providing an organic solution containing an active material and a degradable polymeric material; (c) mixing the aqueous solution with the organic solution to obtain an emulsification solution, wherein the emulsification solution contains a number of microspheres formed by combining the degradable polymeric material with the active material; (d) introducing the emulsification solution into a solidification solution, so as to solidify the microspheres; and (e) employing an aforementioned collection unit to collect the microspheres. The collection unit comprises a tank and a first plate. The tank has an outlet. The plate is removably disposed in the tank. When being lay across the tank, the first plate has its two ends came in contact with the sidewall of the tank so as to divide the tank into a first chamber and a second chamber. The outlet is located in the second chamber. After the solution containing the microspheres is input to the tank through the first chamber, the microspheres are deposited around the first plate, and the solution is caused to pass through or over the first plate to the second chamber and output from the outlet.

The above and other aspects of the invention will become better understood with regard to the following detailed description of the preferred but non-limiting embodiment(s). The following description is made with reference to the accompanying drawings.

BRIEF DESCRIPTION OF THE DRAWINGS

FIG. 10A shows the results of drug release efficiency about Olanzapine microspheres.

FIG. 11A shows the results of drug release efficiency about Granisetron microspheres.

DETAILED DESCRIPTION OF THE INVENTION

Figure 1:
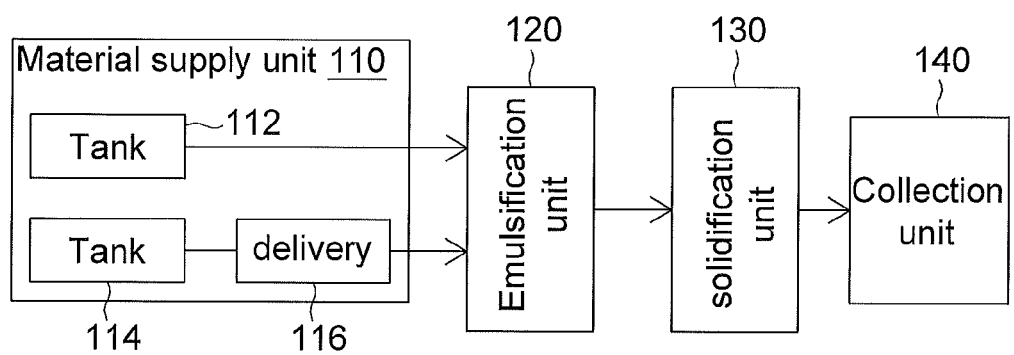
FIG. 1 is a block diagram showing a device for continuously preparing microspheres according to an embodiment of the invention.

The invention discloses a method and a device for continuously preparing microspheres, wherein a collection unit is used to collect the microspheres by a nature process of deposition, thereby not only preventing the problems of deformation and aggregation of the microspheres, but making it possible to continuously collect the microspheres which establishes a process for continuously preparing microspheres. The following description is made with reference to several exemplary embodiments and accompanying drawings. However, it is apparent for those skilled in the art that the description and drawings are made as an exemplary embodiment in accordance with the concept of the invention, and the invention is not limited thereto.
Device for Continuously Preparing Microspheres FIG. 1 is a block diagram showing a device for continuously preparing microspheres according to an embodiment of the invention. In the embodiment of the invention, the device is provided for continuously preparing microspheres, and the device includes a material supply unit 110, an emulsification unit 120, a solidification unit 130, and a collection unit 140, detailed description of which will be provided as follows.

The material supply unit 110 includes two independent tanks 112 and 114 which store different kinds of materials, such as an aqueous solution and an organic solution. The aqueous solution contains a surfactant, and the organic solution contains an active material and a degradable polymeric material. The stored materials in the tanks can be continuously output. For example, the tanks can be elevated to a higher position than that of a delivery pipeline, so that the solution can be continuously introduced into the delivery pipeline. Alternatively, a pump can be installed to draw out the solution from the tanks. The material supply unit 110 further includes a delivery 116 which can control the delivery rate for the two tanks individually or jointly. The delivery 116 is for example a peristaltic pump, a centrifugal pump, a reciprocating pump, a flow rate controller of a drip chamber, a flow rate control valve, or other flow rate control apparatus, with which the mixed proportions of several materials can be adjusted accordingly. The material supply unit 110 is for independently and continuously providing the required materials for preparing microspheres, or preferably for adjusting the rate at which materials are supplied so as to adjust their mixed proportions.

The emulsification unit 120 accepts the aqueous solution and the organic solution, and mixing the aqueous solution with the organic solution to obtain an emulsification solution. The emulsification unit 120 is for example a homogenizer, a blender, or other stir apparatus. The emulsification solution contains a number of microspheres formed by combining the degradable (or biodegradable) polymeric material with the active material.

The solidification unit 130 accepts the emulsification solution and mixing the emulsification solution with a solidification solution. The solidification unit 130 can include a container loaded with a large amount of solidification solution and a stir apparatus, which can introduce the emulsification solution containing microspheres into the solidification solution so as to solidify the microspheres, and can disperse the microspheres through continuous stirring and mixing so as to prevent their aggregation. Besides, the solidifying unit 130 can include a vacuum pump, with which the container loaded with mixed solution can be processed under vacuum condition when being moved to a closed space, thereby accelerating evaporation of the organic solution.

The collection unit 140 accepts the mixed solution containing microspheres, and collects the microspheres by a nature process of deposition, detailed structure of which will be made in other paragraphs.

Based on different production scales of the device for preparing microspheres, the device can have each of its units implemented with different apparatuses. In the description a lab-scale of the device for preparing microspheres is made as an example with reference to FIG. 2, which is a special diagram schematically showing a device for continuously preparing microspheres according to an embodiment of the invention. However, it is practicable for those skilled in the art to make appropriate modification and adjustment according to different production scales or control methods.

Figure 2:
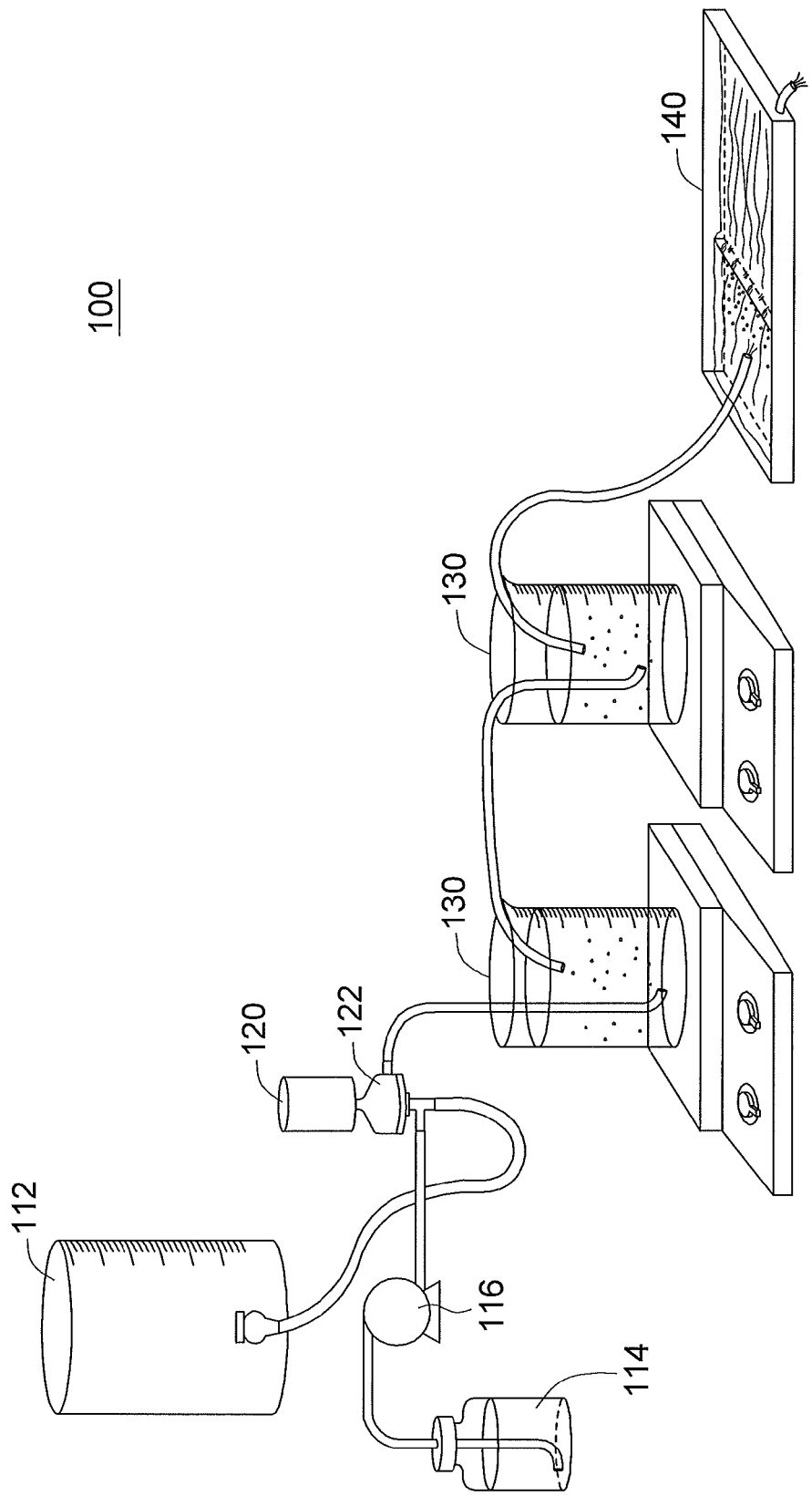
FIG. 2 is a special diagram schematically showing a device for continuously preparing microspheres according to an embodiment of the invention.

Referring to FIG. 2, the tank 112 is a container having a control valve, and loaded with an aqueous solution containing a surfactant. The tank 114 is a wide mouth bottle loaded with an active material and a degradable polymeric material. The tank 112 is disposed on a place higher than that of the delivery pipeline, and has a control valve, so that the aqueous solution can automatically flow into the delivery pipeline at a flow rate controlled by the control valve. The tank 114 is connected to a peristaltic pump 116 for adjusting the flow rate of the organic solution.

The aqueous solution and the organic solution are both input to the emulsification unit 120, so as to form microspheres. The emulsification unit 120 is an emulsion chamber with a homogenizer (IKA, UTL25 digital with S25 KV-25GIL knife). The emulsification unit 120 has an input terminal of Y-shaped tube, which has one part served as the inlet of the aqueous solution, another one served as the inlet of the organic solution, and the other one connected to the emulsification chamber 122. The aqueous solution and the organic solution are pre-mixed in the Y-shaped tube, and introduced into the solidification unit 130 to form an emulsification solution. The emulsification unit 120 has an output terminal connected to the solidification unit 130.

The solidification unit 130 is a set of two 4-liter beakers flowably connected with each other. Each beaker has a stir system designed to disperse the microspheres to prevent aggregation. In addition, a vacuum pump (not shown) can be further connected to the solidification unit 130 to accelerate evaporation of the organic solution. The solidification unit 130 has its former end connected to the emulsification unit 120, and its latter end connected to the collection unit 140.

Figure 3A:
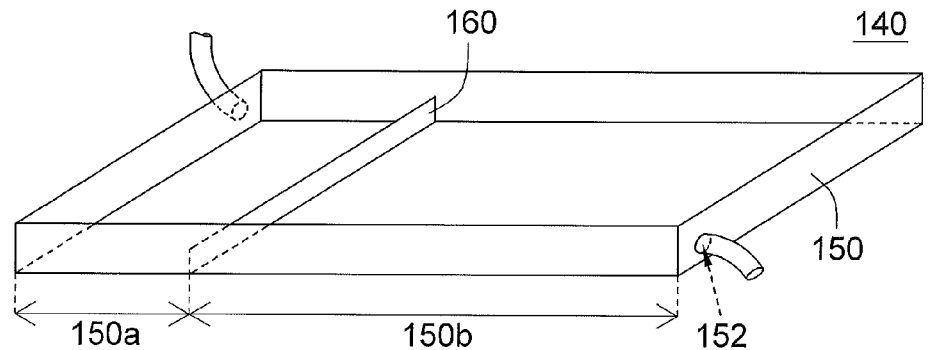
FIG. 3A is a spatial diagram schematically showing a collection unit according to an embodiment of the invention.
Figure 3B:
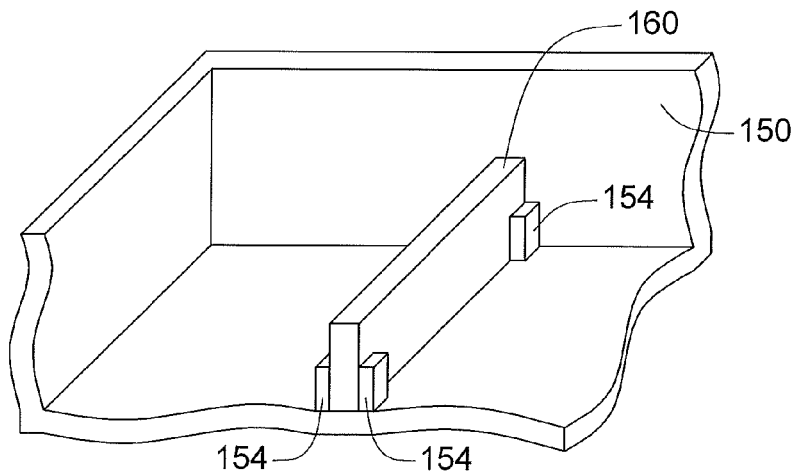
FIG. 3B is a partially enlarged diagram showing a collection unit according to an embodiment of the invention.

FIG. 3A is a spatial diagram schematically showing a collection unit according to an embodiment of the invention. FIG. 3B is a partially enlarged diagram showing a collection unit according to an embodiment of the invention. Referring to FIG. 3A, the collection unit 140 includes a tank 150 and a first plate 160. The first plate 160 is removably disposed in the tank 150. When being lay across the tank 150, the first plate 160 has its two ends came in contact with the sidewall of the tank 150 so as to divide the tank 150 into a first chamber 150a and a second chamber 150b. The tank 150 has an outlet 152. The outlet 152 is located in the second chamber 150b.

FIG. 3B is a partially enlarged diagram showing a collection unit according to an embodiment of the invention. Referring to FIG. 3B, the first plate 160 has its two ends came in contact with the two sidewalls of the tank 150, while there are two side strips 154 disposed on each sidewall. The side strips 154 are fixed on each sidewall of the tank 150. The two side strips 154 on the same sidewall have a distance substantially equivalent to the width of the first plate 160. Although the first plate 160 is not immovably connected to the tank 150, the first plate 160 can be inserted in the tank 150 through the side strips 154, and sandwiched between the side strips 154, making it difficult to change the position of the first plate 160. The first plate 160 can be taken out from the tank 150 when being upwardly moved. In this way, the first plate 160 can be removably disposed in the tank 150. However, it is apparent for those skilled in the art that there are still other practicable ways to removably dispose the first plate in the tank, and the invention is not limited thereto.

The first plate 160 has a lower edge came in closely contact with the bottom surface of the tank 150. The first plate 160 has a height preferably smaller than the height of the tank 150. When the solution containing microspheres is introduced into the tank 150 through the first chamber 150a, the microspheres are blocked or naturally deposited in front of the first plate 160, i.e. between the inlet and the first plate 160. In the meanwhile, the solution is caused to pass through or over the first plate 160 to the second chamber 150b, and output from the outlet 152. Because the solution is caused to flow out the tank 150 from the outlet 152, there is enough room in the tank 150 into which the solution can be continuously introduced.

In this way, the mixed solution containing solidified microspheres can be continuously introduced into the collection unit 140, while the microspheres can be continuously remained in the tank 150 and collected. In the course of collecting microspheres, this embodiment makes use of a nature process of deposition that suspended substances are attracted to gravity, and at least one plate which is so disposed in the flow path of the solution that the microspheres can be blocked and deposited more quickly on the bottom of the tank. Therefore, such a collecting course makes unnecessary any operator's manipulation and any precision instrument or expensive consumables.

Besides, in or after the step of collecting microspheres, a washing solution such as a de-ionized solution can be introduced into the tank 140, and the washing solution can be output from the outlet 152 in a similar manner mentioned above. The washing solution can take away the active material or organic solution from the surface of the microspheres without having the problems of deformation and aggregation of microspheres, so that the product quality is enhanced.

After the microspheres in the solidification unit 130 are deposited on the bottom of the tank 150 and the solution is clearly removed, the first plate 160 can be detached, and a small amount of de-ionized water can be used to suspend the microspheres for collection. Then, the collected microspheres are made into powder by lyophilization.

The collection unit 140 in this embodiment is served as a fundamental model in which a plate is disposed in the flow path of the solution so that the solution, after being introduced into the tank and before output from the outlet, requires to flow through the plate, thereby achieving the effect of blocking microspheres and forcing them to deposit. The collection unit can also be implemented in other manners, such as in a manner of modifying the position, number, combination, or distance of one or more plates for achieving same or better effect. A number of different embodiments are made with reference to corresponding drawings for illustrating the collection unit as follows.

First Collection Unit

Figure 4:
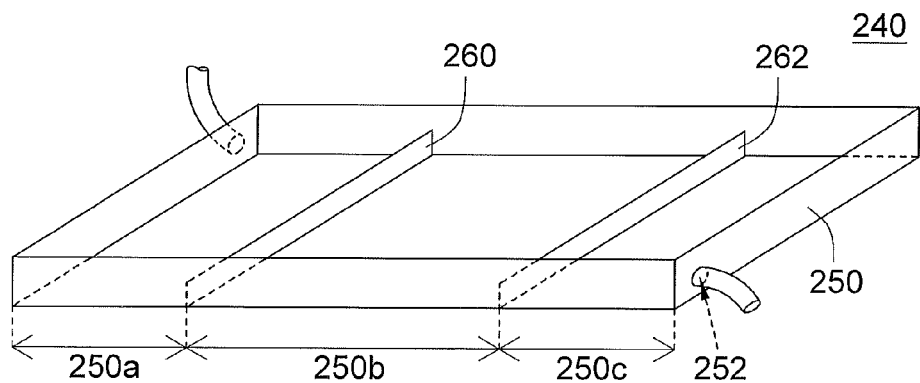
FIG. 4 is a spatial diagram schematically showing a first collection unit according to an embodiment of the invention.

FIG. 4 is a spatial diagram schematically showing a first collection unit according to an embodiment of the invention. The collection unit 240 includes a tank 250, a first plate 260, and a second plate 262. The first plate 260 and the second plate 262 both can be removably disposed in the tank 250. When being lay across the tank 250, each of the first plate 260 and the second plate 262 has its two ends came in contact with the sidewall of the tank 250 so as to divide the tank 250 into a first chamber 250a, a second chamber 250b, and a third chamber 250c. The tank 250 has an outlet 252 located in the third chamber 250c.

After the solution containing microspheres is input to the tank 250 through the first chamber 250a, most of the microspheres are blocked or naturally deposited in front of the first plate 260, and the solution is caused to pass over the first plate 260 to the second chamber 250b. A small portion of the microspheres are blocked or naturally deposited in front of the second plate 262, and the solution is caused to pass over the second plate 262 to the third chamber 250c and output from the outlet 252. Because the collection unit 240 has an increased number of plates, there is a higher chance that microspheres introduced from the solidification unit can be blocked and remained in the tank, and can be collected more completely.

Second Collection Unit

Figure 5:
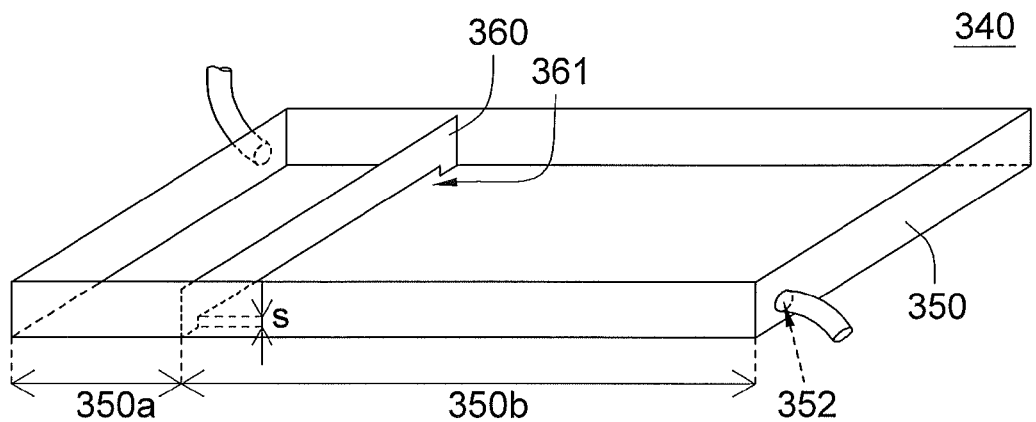
FIG. 5 is a spatial diagram schematically showing a second collection unit according to an embodiment of the invention.

FIG. 5 is a spatial diagram schematically showing a second collection unit according to an embodiment of the invention. The collection unit 340 includes a tank 350 and a first plate

360. The first plate 360 can be removably disposed in the tank 350. When being lay across the tank 350, the first plate 360 has its two ends came in contact with the sidewall of the tank 350 so as to divide the tank 350 into a first chamber 350a and a second chamber 350b. The tank 350 has an outlet 352 located in the second chamber 350b.

The first plate 360 has a lower edge with a slot 361. The first plate 360 has its lower edge separated from a bottom surface of the tank 350 by a distance S when the first plate 360 is disposed in the tank 350. After the solution containing microspheres is input to the tank 350 through the first chamber 350a, most of the microspheres are blocked or naturally deposited around the first plate 360, especially an area of shallow water of the tank 350 where microspheres can be deposited more quickly. In the meanwhile, the solution is caused to pass through the first plate 360 to the second chamber 350b, and output from the outlet 352. In the collection unit 340, the slot 361 is used to create a small area of shallow water between the first plate 360 and the tank 350, and the slot 361 is disposed on a place where the mixed solution flows through, so that microspheres can be deposited more quickly.

Third Collection Unit

Figure 6:
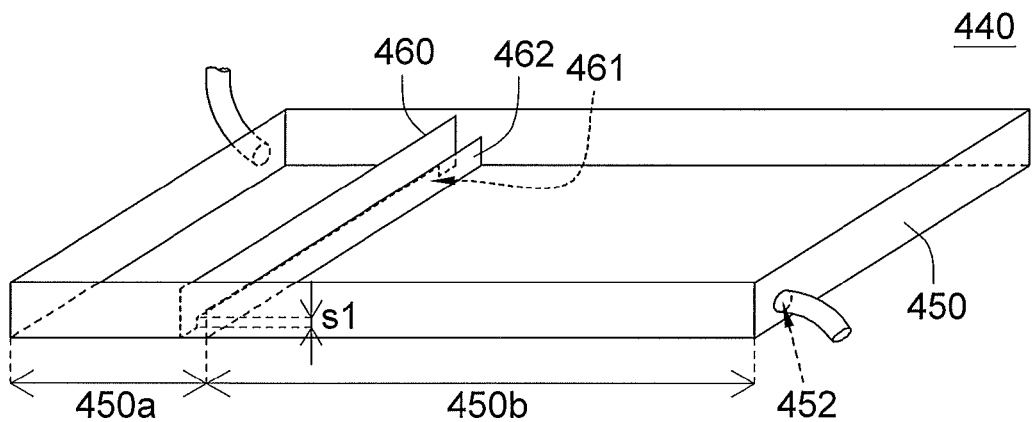
FIG. 6 is a spatial diagram schematically showing a third collection unit according to an embodiment of the invention.

FIG. 6 is a spatial diagram schematically showing a third collection unit according to an embodiment of the invention. The collection unit 440 includes a tank 450, a first plate 460, and a second plate 462. Each of the first plate 460 and the second plate 462 can be removably disposed in the tank 450. When being lay across the tank 450, each of the first plate 460 and the second plate 462 has its two ends came in contact with the sidewall of the tank 450.

The first plate 460 has a lower edge with a slot 461. The first plate 460 has its lower edge separated from a bottom surface of the tank 450 by a distance S when the first plate 460 is disposed in the tank 450. The second plate 462 has a lower edge came in closely contact with the bottom surface of the tank 450. The second plate 462 has a height smaller than the height of the tank 450.

The first plate 460 and the second plate 462 are adjacent to each other. The first plate 460 is disposed on a side adjacent to an inlet, and the second plate 462 is disposed on a side adjacent to an outlet 452. The mixed solution is caused to sequentially flow through the first plate 460 and the second plate 462. The first plate 460 and the second plate 462 divide the tank 450 into a first chamber 450a and a second chamber 450b. The tank 450 has the outlet 452, and the outlet 452 is located in the second chamber 450b.

After the solution containing microspheres is input to the tank 450 through the first chamber 450a, most of the microspheres are blocked or naturally deposited around the first plate 460. A small portion of the microspheres are forced to decelerate. The decelerated microspheres can be much easily blocked or deposited by the second plate 462 adjacent thereto. Then, the solution is output from the outlet 452. The collection unit 440 can be implemented by a combination of different kinds of plates, whose spatial arrangement such as the arrangement of position, slot, distance, or height can be advantageous to deposition of microspheres.

Forth Collection Unit

Figure 7:
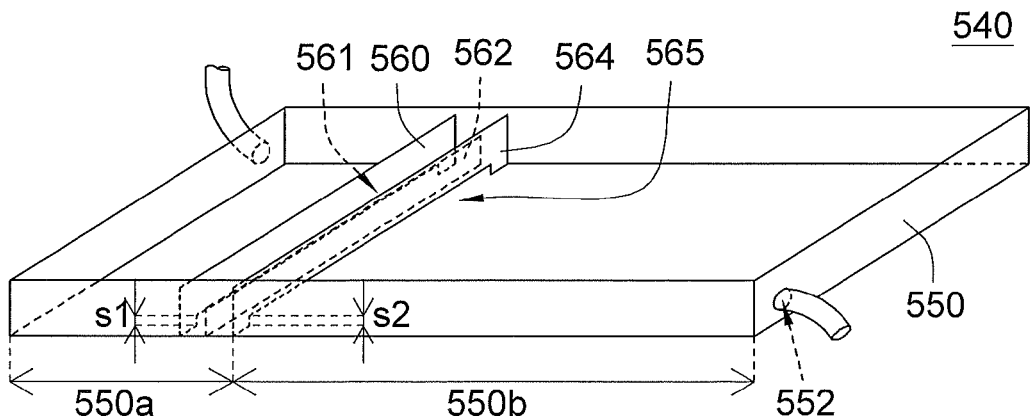
FIG. 7 is a spatial diagram schematically showing a forth collection unit according to an embodiment of the invention.

FIG. 7 is a spatial diagram schematically showing a forth collection unit according to an embodiment of the invention. The collection unit 540 includes a tank 550, a first plate 560, a second plate 562, and a third plate 564. Each of the first plate 560, the second plate 562, and the third plate 564 can be removably disposed in the tank 550. When being lay across the tank 550, each of them has its two ends came in contact with the sidewall of the tank 550.

The first plate 560 has a lower edge with a slot 561. The first plate 560 has its lower edge separated from a bottom surface of the tank 550 by a distance S1 when the first plate 560 is disposed in the tank 550. The second plate 562 has a lower edge came in closely contact with the bottom surface of the tank 550. The second plate 562 has a height smaller than the height of the tank 550. The third plate 564 has a lower edge with a slot 565. The third plate 564 has its lower edge separated from the bottom surface of the tank 550 by a distance S2 when the third plate 560 is disposed in the tank 550. The distances S1 and S2 each can be for example within a range of 1-5 millimeters.

The first plate 560, the second plate 562, and the third plate 564 are adjacent to each other, so as to divide the tank 550 into a first chamber 550a and a second chamber 550b. The tank 550 has an outlet 552 located in the second chamber 550b.

Refer to the corresponding position of the plates shown in FIG. 7. After the solution containing microspheres is input to the tank 550, the solution is caused to sequentially flow through the first plate 560, the second plate 562, and the third plate 564. After the solution containing microspheres is input to the tank 550 through the first chamber 550a, most of the microspheres are blocked or naturally deposited around the first plate 560. A portion of the microspheres are forced to decelerate when passing through the slot 561. The decelerated microspheres can be much easily blocked or deposited by the adjacent second plate 562. Even if a small portion of the microspheres may pass over the second plate 562 to the third plate 564, they are deposited or forced to decelerate when passing through an area of shallow water created by the slot 565. Then, the solution is output from the outlet 552. The collection unit 540 can be implemented by a combination of different kinds of plates, whose spatial arrangement such as the arrangement of position, slot, distance, or height can be advantageous to deposition of microspheres.

Fifth Collection Unit

Figure 8:
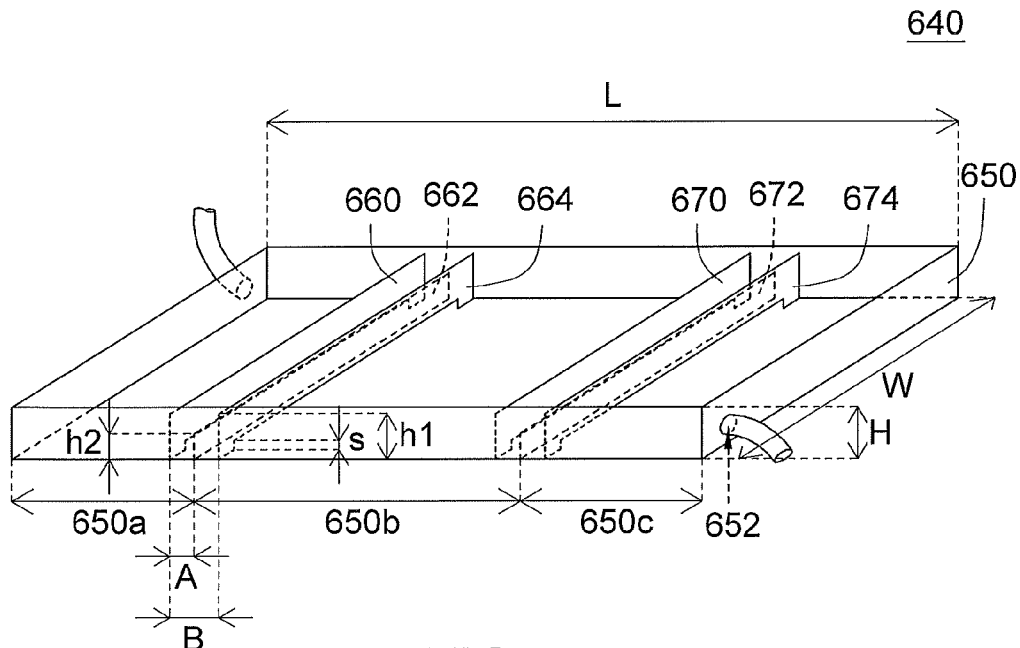
FIG. 8 is a spatial diagram schematically showing a fifth collection unit according to an embodiment of the invention.

FIG. 8 is a spatial diagram schematically showing a fifth collection unit according to an embodiment of the invention. The collection unit 640 includes a tank 650, a first plate 660, a second plate 662, a third plate 664, a forth plate 670, a fifth plate 672, and a sixth plate 674. The tank 650 has an inlet and an outlet separated from each other. The inlet is located at a place around a pipeline shown on the left side of FIG. 8. The first to sixth plates 660-674 are arranged along a direction from the inlet to an outlet 652. All the plates can be removably disposed in the tank 650. When being lay across the tank 650, each of the plates has its two ends came in contact with the sidewall of the tank 650.

The first plate 660, the second plate 662, and the third plate 664 are adjacent to each other when disposed in the tank 650, while the forth 670, the fifth plate 672, and the sixth plate 674 are adjacent to each other when disposed in the tank 650. The two sets of plates divide the tank 650 into a first chamber 650a, a second chamber 650b, and a third chamber 650c. The tank 650 has the outlet 652 located in the third chamber 650c.

The first plate 660 has a lower edge with a slot. The first plate 660 has its lower edge separated from a bottom surface of the tank 650 by a distance S when the first plate 660 is disposed in the tank 650. The second plate 662 has a lower edge came in closely contact with the bottom surface of the tank 650. The second plate 662 has a height smaller than the height of the tank 650. The third plate 664 has its lower edge separated from the bottom surface of the tank 650 by the distance S when the third plate 664 is disposed in the tank 650. Correspondingly, the forth plate 670 has a lower edge with a slot. The forth plate 670 has its lower edge separated from the bottom surface of the tank 650 by the distance S when the forth plate 670 is disposed in the tank 650. The fifth plate 672 has a lower edge came in closely contact with the bottom surface of the tank 650. The fifth plate 672 has a height smaller than the height of the tank 650. The sixth plate 674 has its lower edge separated from the bottom surface of the tank 650 by the distance S when the sixth plate 674 is disposed in the tank 650.

Refer to the corresponding position of the plates shown in FIG. 8. After the solution containing microspheres is input to the tank 650, the solution is caused to sequentially flow through the first plate 660, the second plate 662, the third plate 664, the forth plate 670, the fifth plate 672, and the sixth plate 674. After the solution containing microspheres is input to the tank 650 through the first chamber 650a, most of the microspheres are blocked or naturally deposited around the first plate 660. When passing through the slot of the first plate 660, a portion of the microspheres are forced to decelerate, and are much easily blocked or deposited by the adjacent second plate 662. Even if some microspheres may pass over the second plate 662 to the third plate 664, they are deposited or forced to decelerate when passing through the slot of the third plate 664. Next, the solution containing a small amount of microspheres is caused to flow through the forth plate 670, the fifth plate 672, and the sixth plate 674 which have the same arrangement as the former three plates, so that the small amount of remained microspheres can be blocked or deposited. Then, the solution is output from the outlet 652. The collection unit 640 can be implemented by two sets of plates, each set of plates is a combination of different plates, and whose spatial arrangement such as the arrangement of position, slot, distance, or height can be advantageous to deposition of microspheres. Moreover, because of the use of multiple sets of plates, there is a higher chance that microspheres can be blocked and remained in the tank, and collected more completely.

Specifically, in this embodiment, the tank 650 can be for example a rectangular container. The container has a length L within a range of 300-500 millimeters (mm), and a width W within a range 200-400 mm, and a height H within a range of 30-50 mm. The container can also have an outlet 652 which is located on its sidewall and has a diameter within a range of 5-15 mm. The inlet can be a pipeline directly placed into the container, or an opening which is located on the sidewall of the container and has a diameter within the same range of 5-15 mm. The outlet 652, or the inlet, has its lower edge separated from the bottom surface of the container 650 by a distance within a range of 10-20 mm. The height H of the container is higher than the height h1 of the first plate 660, and the height h1 of the first plate 660 is higher than the height h2 of the second plate 662. The first plate 660 can have its height h1 within a range of 20-40 mm, and second plate 662 can have its height h2 within a range within a range of 10-20 mm. The distance A between the first plate 660 and the second plate 662 is about 5 mm. The distance B between the first plate 660 and the third plate 664 is about 10 mm. The distance S by which the slot of the third plate 664 is separated from the bottom surface of the tank is within a range of 1-5 mm. The distance X by which the slot of the third plate 664 is separated from the sidewall of the tank is within a range of 1-10 mm. The aforementioned description provides the information relative to the size of each part of the collection unit, which is made as an exemplified example without any intent of limitation and is apparent for those skilled in the art to appropriately modify and adjust the size, shape, disposed distance, and arrangement of the tank or the plate in order to meet different requirements.

Method for Continuously Preparing Microspheres

Figure 9:
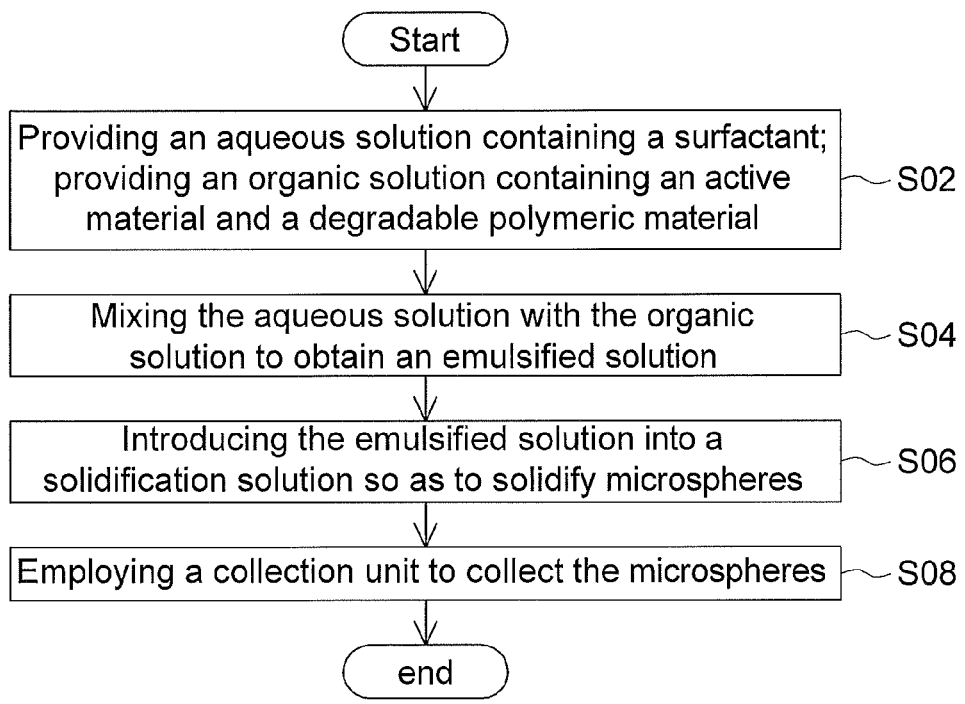
FIG. 9 is a flow chart showing a method for continuously preparing microspheres according to an embodiment of the invention.

The invention further provides a method for continuously preparing microspheres by using the aforementioned device. FIG. 9 is a flow chart showing a method for continuously preparing microspheres according to an embodiment of the invention. The method includes the following steps. First, in the step S02, an aqueous solution containing a surfactant is provided, and an organic solution containing an active material and a degradable polymeric material is provided. The degradable polymeric material is for example a biodegradable polymer, poly(lactic/glycolic acid) (PLGA). The active material is for example Olanzapine or Granisetron. The aqueous solution and the organic solution have a mixing ratio of 200:1, for example.

Next, as shown in step S04, the aqueous solution is mixed with the organic solution to obtain an emulsification solution. The emulsification solution contains a number of microspheres formed by combining the degradable polymeric material with the active material. Then, as shown in step S06, the emulsification solution is introduced into a solidification solution, so as to solidify the microspheres. The solidification solution is for example polyvinyl alcohol (PVA). After that, as shown in step S08, a collection unit is employed to collect the microspheres, wherein the collection unit can be at least one or any combination of the collection units 140, 240, 340, 440, 540, and 640. Alternatively, a washing solution can also be introduced into the tank, wherein the washing solution is caused to have contact with the microspheres, and output form the outlet in a similar manner.

Because the solution is caused to flow out the tank from the outlet, there is enough room in the tank 150 into which the solution can be continuously introduced. In this way, the mixed solution containing solidified microspheres can be continuously introduced into the collection unit, while the microspheres can be continuously blocked or deposited in the tank and collected. In addition, the collection of microspheres makes use of a nature process of deposition that suspended substances are attracted to gravity, and at least one plate which is so disposed in the flow path of the solution that the microspheres can be blocked and deposited on the bottom of the tank. Such a collecting course makes unnecessary any operator's manipulation, so that the courses from production to collection can be integrated into a continuous process, which has great potential for mass production scale.

In addition, the aforementioned device and method can prevent the problems of deformation and aggregation of the prepared microspheres, and the active material can be released over an extended period of time. Several experimental results are provided below for validation. However, it is apparent for those skilled in the art that the device and the method for continuously preparing microspheres disclosed in this invention can be not only applied to those types of drug and polymer mentioned below, but to microspheres or microcapsules made by other materials.

Preparing Olanzapine Microsphere

Materials: Lactide/glycolide copolymer (molar ratio 85/15), having an inherence viscosity of 0.84 dl/g (chloroform. 25° C., c=0.1 g/dl), is purchased from PURAC. Water-soluble Vitamin E, tocopheryl polyethylene glycol succinate (TPGS), containing 278 mg/g tocopherol, and Olanzapine both are USP NF grade. Polyvinyl alcohol (PVA), having an average molar weight of 30,000-70,000, is used as the surfactant of organic/water (o/w) emulsion, and is supplied by Sigma-Aldrich. The organic solution is prepared as follows. The PLGA, Olanzapine and TPGS are dissolved in 10 milliliter (ml) dichloromethane, which is used as the organic phase in o/w emulsion process. Each milliliter of dichloromethane contains 160 mg PLGA, 64 mg Olanzapine, and 40 mg TPGS. Based on a 0.5% of o/w ratio, water phase is prepared of 0.1% PVA aqueous at 6-8° C.

Method and Microspheres Appearance: The device for continuously preparing microspheres is the one shown in FIG. 2. The collection unit is the one shown in FIG. 8. An 80 ml organic solution and a 16,000 ml aqueous solution are delivered at 1.25 ml/min and 250 ml/min, respectively to the emulsification unit. The emulsification unit is an emulsion chamber with a homogenizer (IKA, UTL25 digital with S25 KV-25GIL knife). The emulsification unit has an input terminal of Y-shaped tube, which has one part served as the inlet of the aqueous solution, another one served as the inlet of the organic solution, and the other one connected to the emulsification chamber. The two phases are premixed in Y-tube and then introduced into the emulsion chamber. The homogenizer is pre-set at a rate of 8000 rpm. In the following steps, the emulsification solution is introduced into the solidification unit. The solidification unit is a set of two 4-liter beakers flowably connected with each other. Each beaker has its microspheres stirred at a rate of 500 rpm by a stir element. After solidification, the microspheres are collected in the collection unit 640, washed by using 0.1% F-68 aqueous solution twice, and de-ionized solution once. Finally, the product is made into powder by lyophilization.

Test to Drug Release Efficiency

As to the obtained microspheres, a 20 mg portion of the prepared microspheres, Olanzapine-TPGS-PLGA microspheres, is introduced in a 50 ml centrifuge tube, and dissolved in a 12 ml PBS solution (0.01M, containing 0.01% Tween 80 and 0.01% sodium azide). The tube is shaken at 60 rpm in the water bath at 37° C. Samples are analyzed periodically within 8 weeks by the HPLC (270 nm) to analyze the drug release rate.

Figure 10B:
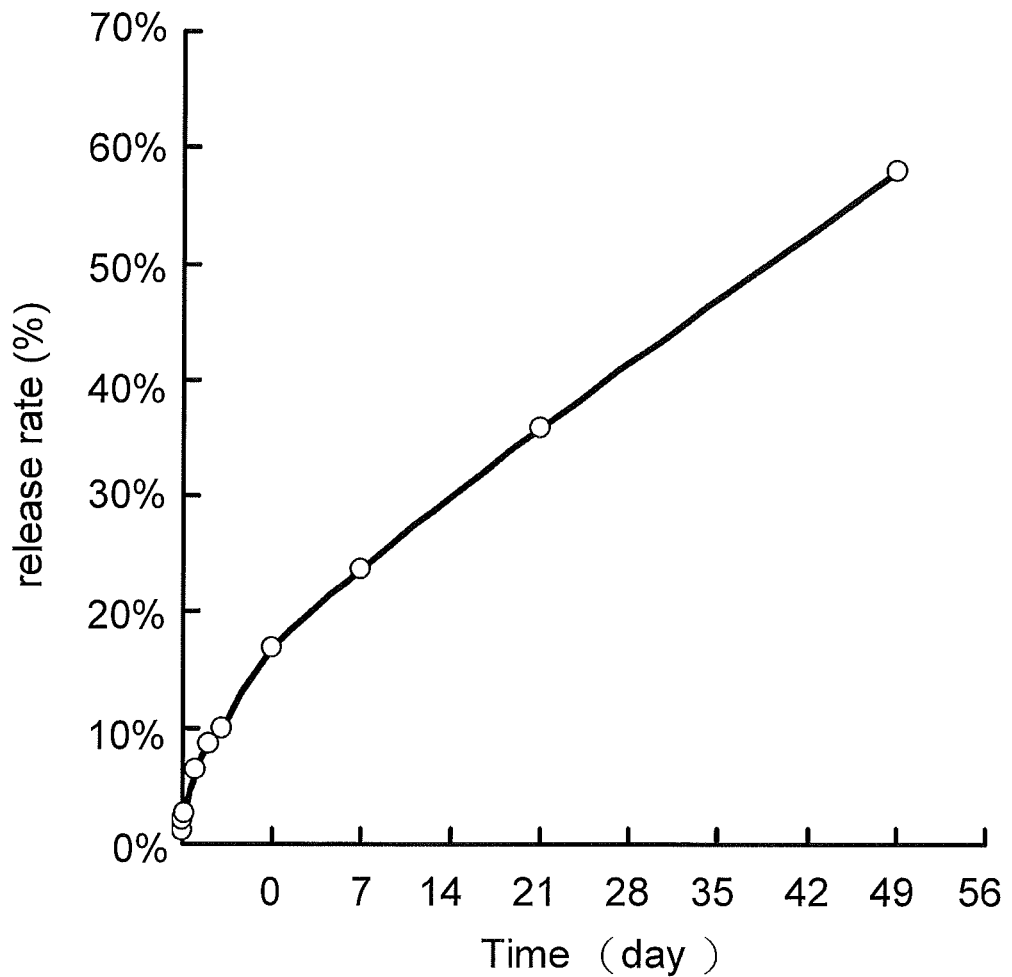
FIG. 10B is a curve diagram showing the results of drug release efficiency about Olanzapine microspheres.

The results of in vitro test to drug release rate about Olanzapine microspheres are shown in FIGS. 10A and 10B. As to the microspheres prepared by the device and the method according to the embodiments of the invention, the results show that the release rate is stable from the start of dispensing the drug. Therefore, the drug has less initial effect, and the overall variation of drug release efficiency reveals that the drug is released constantly, almost linearly. In other words, the drug can be released in body at a constant rate, complied with a regulation of zero-order release kinetics, and close to a zero-order release model of drugs. Constant release can reduce the fluctuation of drug concentration within blood, and increase a patient's adaptability to take drugs.

Preparing Granisetron Microsphere

Materials: PLGA (molar ratio 50/50), TPGS, Granisetron, and PVA. The organic solution is prepared as follows. The PLGA, Granisetron and TPGS are dissolved in 10 milliliter (ml) dichloromethane, which is used as the organic phase in o/w emulsion process. Each milliliter of dichloromethane contains 160 mg PLGA, 16 mg Granisetron, and 10 mg TPGS. Based on a 0.5% of o/w ratio, water phase is prepared of 0.1% PVA aqueous at 6-8° C.

Method and Microspheres Appearance: The preparing method is the same as that in the previous example. The particle size of microsphere is about 20.5 micrometers. The encapsulation efficiency is about 81%.

Test to Drug Release Efficiency

As to the obtained microspheres, a 20 mg portion of the prepared microspheres, Granisetron-TPGS-PLGA microspheres, is introduced in a 50 ml centrifuge tube, and dissolved in a 12 ml PBS solution (0.01M, containing 0.01% Tween 80 and 0.01% sodium azide). The tube is shaken at 60 rpm in the water bath at 37° C. Samples are analyzed periodically within 5 days by the HPLC (270 nm) to analyze the drug release rate.

Figure 11B:
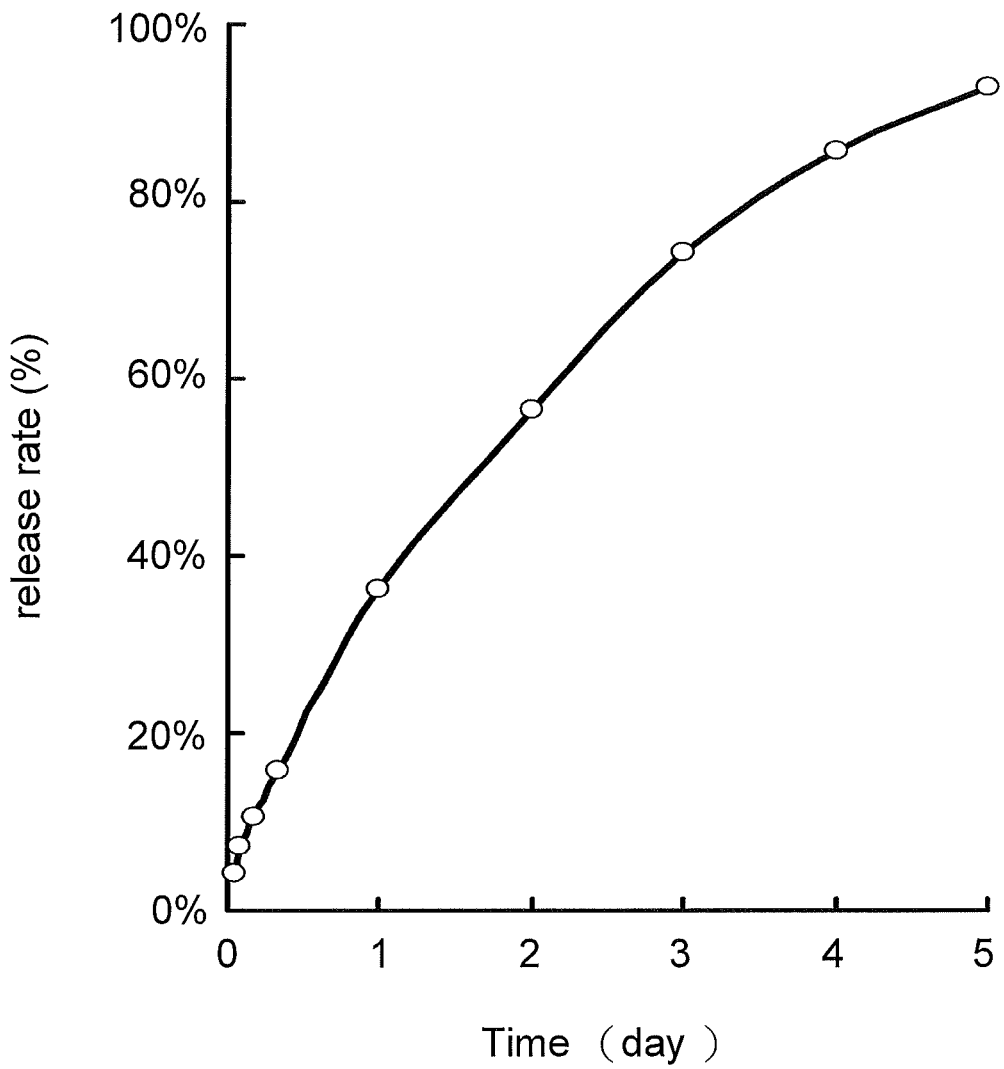
FIG. 11B is a curve diagram showing the results of drug release efficiency about Granisetron microspheres.

The results of in vitro test to drug release rate about Granisetron microspheres are shown in FIGS. 11A and 11B.

According to the method and the device for continuously preparing microspheres as well as the collection unit thereof disclosed above, the mixed solution in the collection unit can be caused to locate at an area of shallow water, or pass through a more shallow area such as an area between the slot of plate and the tank, so that the suspended microspheres can be deposited quickly. The solution can be output continuously from the outlet, and the mixed solution can be continuously introduced into the tank. In this way, the steps of the method which include emulsification, solidification, and collection can be integrated into a continuous process without any operator's manipulation. That is, the embodiment makes it possible to continuously prepare and collect microspheres without any operator's manipulation if the device is installed completely and turned on.

On the other hand, in a conventional method of collection microspheres, the microspheres suspended in the tank are collected by centrifugalization. Such a conventional method belongs to a batch process, which requires an operator to manipulate machinery apparatuses according to a required procedure to complete the steps of collecting microsphere. As compared with the conventional process, the method and the device for continuously preparing microspheres according to the embodiment have the advantages exemplified below.

1. The courses from production to collection can be integrated into a continuous process, which has great potential for mass production scale.
2. The operation of the invention is suitable for a bacteria-free environment. The device disclosed in the embodiment has a moderate size and a simple structure, all units of which can be anti-bacterial, or operated in a bacteria-free environment. The overall process of preparing microspheres can be operated in a bacteria-free environment, sot that the product quality can be increased.
3. The method disclosed in the embodiment can be implemented as a continuous preparing process, which makes it possible to continuously prepare and collect microspheres without any operator's manipulation if the device is installed completely and turned on.
4. According to the device and the method of the embodiment, the prepared microspheres have less initial effect, and have a release model close to zero-order.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A collection unit for collecting a plurality of microspheres in a solution, the collection unit comprising:
   a tank having an outlet; and
   a first plate removably disposed in the tank, the first plate having a lower edge with at least one slot, wherein when the first plate is disposed across the tank,
      the first plate has its lower edge separated, by the slot, from a bottom surface of the tank by a first distance, the first plate has two ends coupled with the sidewall of the tank so as to divide the tank into a first chamber and a second chamber, wherein the outlet is located in the second chamber, and the slot is separated from the sidewall of the tank by a second distance;

wherein after the solution containing the microspheres is input to the tank through the first chamber, the microspheres are deposited around the first plate, and the solution is caused to pass through or over the first plate to the second chamber and output from the outlet.

2. The collection unit according to claim 1, wherein the tank has a height smaller than the inner diameter of the tank.

3. The collection unit according to claim 1, wherein the tank has a height within a range of 30-50 millimeters.

4. The collection unit according to claim 1, wherein the first plate has a height smaller than the height of the tank.

5. The collection unit according to claim 1, wherein the first distance is within a range of 1-5 millimeters.

6. The collection unit according to claim 1, further comprising a second plate having a height smaller than the height of the tank, removably disposed in the tank, and having, when the second plate lays across the tank, two ends coupled with the sidewall of the tank and a lower edge in contact with the bottom surface of the tank, whereby the solution is caused to sequentially flow through the first plate and the second plate.

7. The collection unit according to claim 6, wherein the second plate has a height smaller than the height of the first plate.

8. The collection unit according to claim 6, further comprising a third plate, removably disposed in the tank and having, when the third plate lay across the tank, two ends coupled with the sidewall of the tank and a lower edge separated from the bottom surface of the tank by a third distance, whereby the solution is caused to sequentially flow through the first plate, the second plate, and the third plate.

9. A device for continuously preparing microspheres, comprising:

a material supply unit for independently and continuously providing an aqueous solution and an organic solution, the aqueous solution containing a surfactant, the organic solution containing an active material and a degradable polymeric material;

an emulsification unit for accepting the aqueous solution and the organic solution and mixing the aqueous solution with the organic solution to obtain an emulsification solution, the emulsification solution containing a plurality of microspheres formed by combining the degradable polymeric material with the active material;

a solidification unit for accepting the emulsification solution and mixing the emulsification solution with a solidification solution, so as to solidify the microspheres; and a collection unit, comprising:

a tank for receiving the solution containing the microspheres, the tank having an outlet; and a first plate removably disposed in the tank, the first plate having a lower edge with at least one slot, wherein when the first plate is disposed across the tank, the first plate has its lower edge separated, by the slot, from a bottom surface of the tank by a first distance, the first plate has two ends coupled with the sidewall of the tank so as to divide the tank into a first chamber and a second chamber, wherein the outlet is located in the second chamber, and the slot is separated from the sidewall of the tank by a second distance;

wherein when the solution containing the microspheres is received in the tank through the first chamber, the microspheres are deposited around the first plate, and the solution is caused to pass through or over the first plate to the second chamber and output from the outlet.

10. The device according to claim 9, wherein the emulsification unit is a homogenizer.

11. The device according to claim 9, wherein the material supply unit comprises a delivery for controlling the delivery rate of the organic solution.

12. The device according to claim 11, wherein the delivery is a peristaltic pump, a centrifugal pump, or a reciprocating pump.

13. The device according to claim 9, wherein the solidification unit comprises a vacuum pump.

* * * * *